US012688938B2

(12) United States Patent
Kuo et al.

(10) Patent No.: US 12,688,938 B2
(45) Date of Patent: Jul. 21, 2026

(54) METHOD FOR ESTABLISHING HEART FAILURE ASSESSMENT PROGRAM AND METHOD FOR ASSESSING OCCURRENCE OF HEART FAILURE

(71) Applicant: China Medical University, Taichung City (TW)

(72) Inventors: Chin-Chi Kuo, Taichung City (TW); Sheng-Ya Lu, Taichung City (TW); Hsiu-Yin Chiang, Taichung City (TW); Yu-Ting Lin, Taichung City (TW)

(73) Assignee: China Medical University, Taichung City (TW)

( * ) Notice: Subject to any disclaimer, the term of this patent is extended or adjusted under 35 U.S.C. 154(b) by 110 days.

(21) Appl. No.: 18/499,386

(22) Filed: Nov. 1, 2023

(65) Prior Publication Data

US 2024/0145094 A1 May 2, 2024

Related U.S. Application Data

(60) Provisional application No. 63/421,758, filed on Nov. 2, 2022.

(51) Int. Cl.
*G16H 50/20* (2018.01)
*A61B 5/00* (2006.01)
(Continued)

(52) U.S. Cl.
CPC ............. *G16H 50/20* (2018.01); *A61B 5/346* (2021.01); *A61B 5/7207* (2013.01); *A61B 5/7267* (2013.01); *G16H 50/50* (2018.01)

(58) Field of Classification Search
CPC ........ G16H 50/20; G16H 50/50; A61B 5/346; A61B 5/7207; A61B 5/7267
See application file for complete search history.

(56) References Cited

U.S. PATENT DOCUMENTS 10,582,862 B1 *  3/2020  Selvaraj ................... A61B 5/11
2019/0059763 A1 *  2/2019  Shakur ................... G16H 40/67
(Continued)

FOREIGN PATENT DOCUMENTS

CN     111095429 A     5/2020
CN     112674779 A     4/2021
(Continued)

OTHER PUBLICATIONS

Zhang et al., "A novel machine learning-enabled framework for instantaneous heart rate monitoring from motion artifact-corrupted electrocardiogram signals," Physiol. Meas. 37 (2016) 1945-1967; doi:10.1088/0967-3334/37/11/1945. (Year: 2016).*
(Continued)

*Primary Examiner* — Jonathon A. Szumny

(57) ABSTRACT

A method for assessing occurrence of heart failure includes the following steps. A heart failure assessment program established is provided. A target ECG signal data of the subject is provided, wherein the target ECG signal data includes a plurality of target heartbeat waveform data and a plurality of target heart rate data. A data pre-processing step is performed, wherein the target ECG signal data is pre-processed by the data processing module so as to obtain a processed target ECG signal data. An analyzing step is performed, wherein the processed target ECG signal data is analyzed by the heart failure assessment program so as to obtain a heart failure occurrence assessing result, and the heart failure occurrence assessing result presents a heart failure occurring condition and the severity of the heart failure of the subject.

15 Claims, 8 Drawing Sheets

(51) Int. Cl.
    *A61B 5/346*         (2021.01)
    *G16H 50/50*        (2018.01)

(56)                   References Cited

U.S. PATENT DOCUMENTS

| | | | |
|---|---|---|---|
| 2021/0290175 A1* | 9/2021 | Jayaraman | ............. A61B 5/364 |
| 2021/0334963 A1 | 10/2021 | Isgum et al. | |
| 2022/0039729 A1* | 2/2022 | Fontanarava | ........ A61B 5/7264 |

FOREIGN PATENT DOCUMENTS

| | | | | |
|---|---|---|---|---|
| CN | 113827215 A | * | 12/2021 | ......... A61B 5/02405 |
| CN | 114052744 A | | 2/2022 | |
| CN | 114224355 A | * | 3/2022 | |
| CN | 114724702 A | | 7/2022 | |
| CN | 114869259 A | * | 8/2022 | ............. A61B 5/748 |
| DE | 102015219543 A1 | * | 4/2016 | ......... A61B 5/02416 |

OTHER PUBLICATIONS

Saleem et al., "A two-step pre-processing tool to remove Gaussian and ectopic noise for heart rate variability analysis," Scientific Reports | (2022) 12:18396 | https://doi.org/10.1038/s41598-022-21776-2. (Year: 2022).*

\* cited by examiner

100

110 an ECG signal database is provided 120 a reference data pre-processing step is performed 121 an offset-correcting step is performed 122 a normalizing step is performed 130 a feature analyzing step is performed 140 a training step is performed

300

310 a heart failure assessment program is provided 320 a target ECG signal data of a subject is provided 330 a data pre-processing step is performed 331 a target offset-correcting step is performed 332 a target normalizing step is performed 340 an analyzing step is performed

400

410 — a heart failure assessment program is provided

420 — a target ECG signal data of a subject is provided

430 — a data pre-processing step is performed

431 — a target offset-correcting step is performed

432 — a target normalizing step is performed

433 — a target signal transforming step is performed

434 — a target cardiac axis correcting step is performed

440 — an analyzing step is performed

METHOD FOR ESTABLISHING HEART FAILURE ASSESSMENT PROGRAM AND METHOD FOR ASSESSING OCCURRENCE OF HEART FAILURE

RELATED APPLICATIONS

This application claims priority to U.S. Provisional Application Ser. No. 63/421,758, filed Nov. 2, 2022, which is herein incorporated by reference.

BACKGROUND

Technical Field

The present disclosure relates to a medical information analysis method. More particularly, the present disclosure relates to a method for establishing heart failure assessment program and a method for assessing occurrence of heart failure.

Description of Related Art

With the universal implementation of electronic medical records (EMRs), a large number of clinical information such as patient diagnostic codes, medical imaging and blood tests can be recorded, managed, and analyzed. Also, due to advances in the machine learning technology, many studies have begun to use EMR data to improve the quality of patient care and prevent possible complications.

In the current clinical field, the heart failure is diagnosed according to the medical history and clinical symptoms of the patient and confirmed with the echocardiogram thereof. However, these symptoms may be due to many other possible causes. Importantly, left ventricular diastolic dysfunction can develop without any of the clinical symptoms.

Therefore, how to develop a method that can conveniently and accurately assess the occurrence of the heart failure has become a technical issue with clinical application value.

SUMMARY

According to one aspect of the present disclosure, a method for establishing heart failure assessment program, which is for establishing a heart failure assessment program, includes the following steps. An ECG (electrocardiogram) signal database is provided, wherein the ECG signal database includes a plurality of reference ECG signal data of a plurality of heart failure patients, each of the reference ECG signal data includes a plurality of heartbeat waveform data and a plurality of heart rate data, and each of the plurality of heartbeat waveform data corresponds to one of the plurality of heart rate data. A reference data pre-processing step is performed, wherein each of the plurality of reference ECG signal data is pre-processed by a data processing module so as to obtain a plurality of processed ECG signal data, and the reference data pre-processing step includes the following steps: an offset-correcting step is performed, wherein a baseline of each of the plurality of reference ECG signal data is adjusted based on the plurality of heart rate data corresponding thereto; and a normalizing step is performed, wherein each of the plurality of reference ECG signal data is processed by an interpolation method so as to obtain the plurality of processed ECG signal data. A feature analyzing step is performed, wherein the plurality of processed ECG signal data are analyzed by a machine learning algorithm model so as to obtain at least one heart failure assessing feature. A training step is performed, wherein the at least one heart failure assessing feature is trained to achieve a convergence by the machine learning algorithm model so as to obtain the heart failure assessment program, and the heart failure assessment program is for assessing whether a subject has a heart failure or not and a severity of the heart failure.

According to another aspect of the present disclosure, a method for assessing occurrence of heart failure includes the following steps. The heart failure assessment program established by the method for establishing heart failure assessment program of the aforementioned aspect is provided. A target ECG signal data of the subject is provided, wherein the target ECG signal data includes a plurality of target heartbeat waveform data and a plurality of target heart rate data, and each of the plurality of target heartbeat waveform data corresponds to one of the plurality of target heart rate data. A data pre-processing step is performed, wherein the target ECG signal data is pre-processed by the data processing module so as to obtain a processed target ECG signal data, and the data pre-processing step includes the following steps: a target offset-correcting step is performed, wherein a baseline of the target ECG signal data is adjusted based on the plurality of target heart rate data corresponding thereto; and a target normalizing step is performed, wherein the target ECG signal data is processed by the interpolation method so as to obtain the processed target ECG signal data. An analyzing step is performed, wherein the processed target ECG signal data is analyzed by the heart failure assessment program so as to obtain a heart failure occurrence assessing result, and the heart failure occurrence assessing result presents a heart failure occurring condition and the severity of the heart failure of the subject.

BRIEF DESCRIPTION OF THE DRAWINGS

The present disclosure can be more fully understood by reading the following detailed description of the embodiment, with reference made to the accompanying drawings as follows.

DETAILED DESCRIPTION

The present disclosure will be further exemplified by the following specific embodiments to facilitate utilizing and practicing the present disclosure completely by the people skilled in the art without over-interpreting and over-experimenting. However, these practical details are used to describe how to implement the materials and methods of the present disclosure and are not necessary.

[Method for Establishing Heart Failure Assessment Program of the Present Disclosure]

Figure 1:
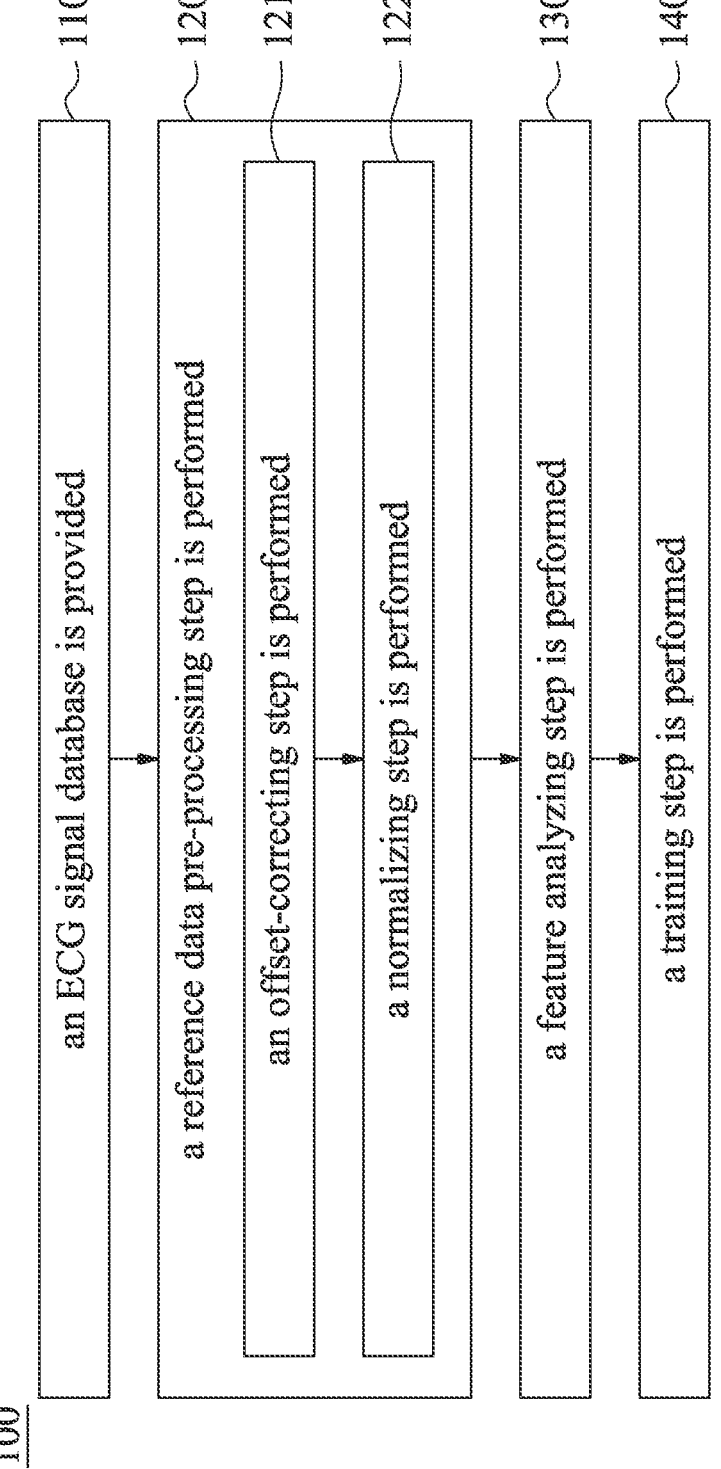
FIG. 1 is a flow chart of a method for establishing heart failure assessment program according to one embodiment of the present disclosure.

Reference is made to FIG. 1, which is a flow chart of a method 100 for establishing heart failure assessment program according to one embodiment of the present disclosure. The method 100 for establishing heart failure assessment program includes Step 110, Step 120, Step 130 and Step 140.

In Step 110, an ECG signal database is provided, wherein the ECG signal database includes a plurality of reference ECG signal data of a plurality of heart failure patients, each of the reference ECG signal data includes a plurality of heartbeat waveform data and a plurality of heart rate data, and each of the heartbeat waveform data corresponds to one of the heart rate data. In detail, the heart failure patients can be systolic dysfunction patients or diastolic dysfunction patients, and one of the heart failure patients can correspond to plural of the reference ECG signal data. Further, a reference ECG signal data obtained closest to the time when the patient received a cardiac ultrasound examination can be used for the following analysis, and the present disclosure is not limited thereto. Furthermore, each of the reference ECG signal data can be a 12-lead electrocardiogram data, and the present disclosure is not limited thereto.

In Step 120, a reference data pre-processing step is performed, wherein each of the reference ECG signal data is pre-processed by a data processing module so as to obtain a plurality of processed ECG signal data. Each of the reference ECG signal data will be pre-processed in the reference data pre-processing step so as to remove the background noise of each of the reference ECG signal data as well as the sampling differences between different reference ECG signal data. In particular, the reference data pre-processing step can include Step 121 and Step 122.

In Step 121, an offset-correcting step is performed. In detail, the ECG signal may have a baseline (also known as "isoelectric potential line") offset due to the sliding of the electrode patches, the breath of the patient or other reasons during the examination. In order to prevent the interferences caused by the offsets of the baseline, a baseline of each of the reference ECG signal data should be corrected. Accordingly, in the offset-correcting step, the baseline of each of the reference ECG signal data is adjusted based on the plurality of heart rate data corresponding thereto so as to eliminate the interference caused by the offsets of the baseline. In particular, each of the reference ECG signal data will be processed by the data processing module with a median filter first, and then the said reference ECG signal data will be processed by LOESS (locally weighted scatterplot smoothing) algorithm, so that the previously processed signal will be smoother. Finally, the smooth signal obtained therefrom will be removed from the reference ECG signal data so as to achieve the correction of the baseline offset. However, it must be noted that other types of filter and algorithm also can be applied in the present disclosure so as to process the reference ECG signal data and then correct the baseline thereof, and the present disclosure is not limited to a specific type of filters and a specific type of algorithms.

In Step 122, a normalizing step is performed, wherein each of the plurality of reference ECG signal data is processed by an interpolation method so as to obtain the plurality of processed ECG signal data. In detail, there is a plurality of heartbeats within a 10-second period in each of the reference ECG signal data, and although the repeatability of the waveforms of different heartbeats is very high, there are still slight differences between the waveforms of different heartbeats. Thus, in the normalizing step, all of the heart rate data in one reference ECG signal data will be averaged by the interpolation method so as to obtain a normalized heart rate data, and the normalized heart rate data obtained therefrom will be used as a heart rate value of the reference ECG signal data so as to normalize all of the heartbeat waveform data thereof. Then, each of the heartbeat waveform data of the reference ECG signal data will be separated out, and all of the heartbeat waveform data will be averaged so as to obtain a normalized heartbeat waveform data. Finally, the normalized heartbeat waveform data is defined as one heartbeat of the reference ECG signal data, and then the processed ECG signal data with a specific heartbeat pattern is obtained.

Further, the interpolation method can be a cubic spline function interpolation method, but the present disclosure is not limited thereto. Furthermore, the data processing module can be any of the data processing modules which can be used to analyze and perform the aforementioned processes to the reference ECG signal data, and the present disclosure is not limited to any type of data processing modules.

In Step 130, a feature analyzing step is performed, wherein the plurality of processed ECG signal data are analyzed by a machine learning algorithm model so as to obtain at least one heart failure assessing feature. In detail, in the feature analyzing step of the present disclosure, the best parameter combination used to train or select the model is obtained by repeatedly testing different combinations of the parameters. In the present disclosure, the machine learning algorithm model can be a gradient descent algorithm model, and the gradient descent algorithm model can be XGBoost machine learning algorithm model. The plurality of processed ECG signal data can be analyzed by the machine learning algorithm model with a grid search method or can be further analyzed with a cross validation method so as to obtain the at least one heart failure assessing feature.

In Step 140, a training step is performed, wherein the at least one heart failure assessing feature is trained to achieve a convergence by the machine learning algorithm model so as to obtain the heart failure assessment program of the present disclosure, and the heart failure assessment program is for assessing whether a subject has a heart failure or not and a severity of the heart failure.

Figure 2:
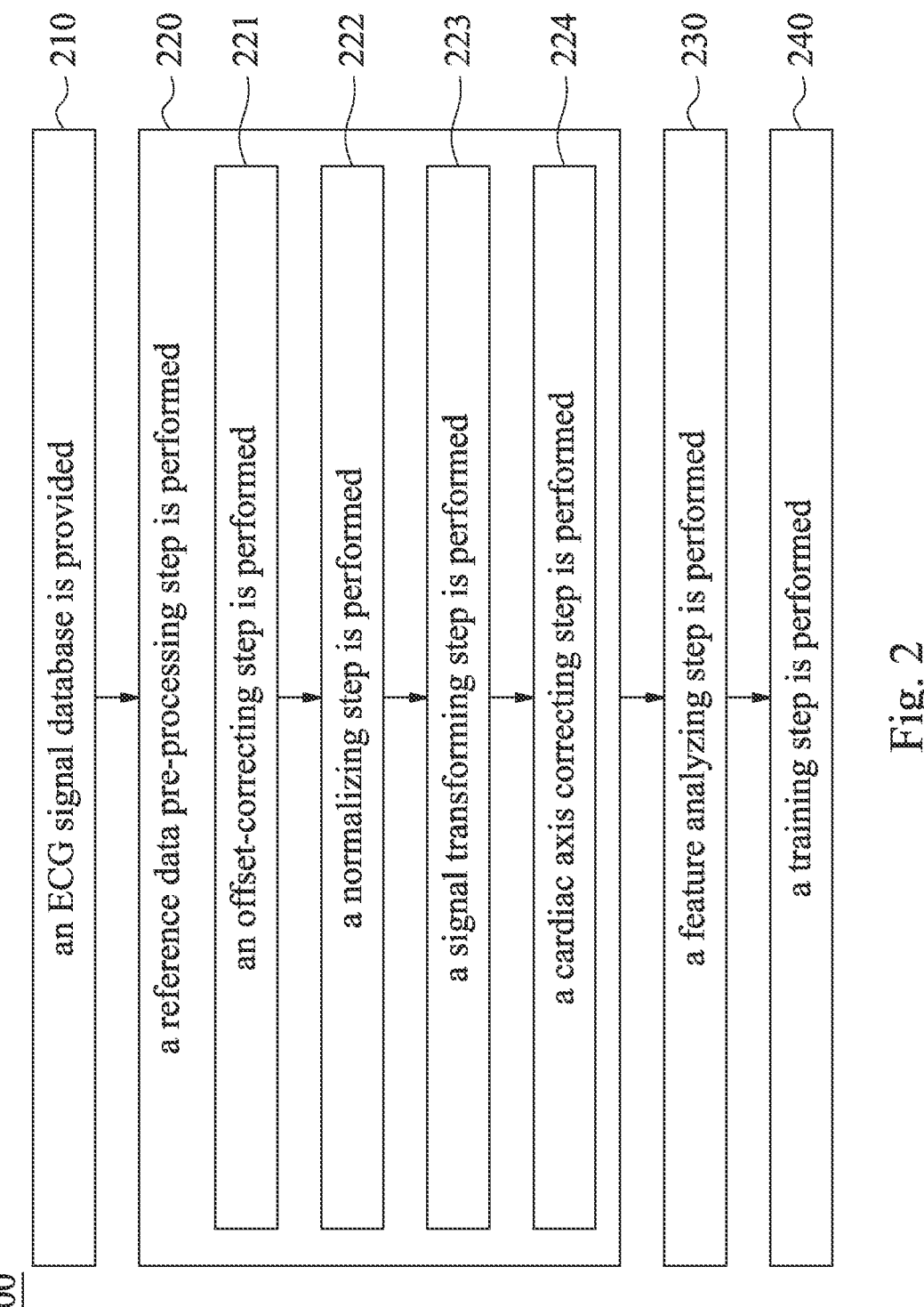
FIG. 2 is a flow chart of a method for establishing heart failure assessment program according to another embodiment of the present disclosure.

Reference is made to FIG. 2, which is a flow chart of a method 200 for establishing heart failure assessment program according to another embodiment of the present disclosure. The method 200 for establishing heart failure assessment program includes Step 210, Step 220, Step 230 and Step 240, wherein Step 210, Step 230 and Step 240 are the same as Step 110, Step 130 and Step 140 of the method 100 for establishing heart failure assessment program of FIG. 1, so that the same details will not be described again herein.

In Step 220, a reference data pre-processing step is performed, wherein each of the reference ECG signal data is pre-processed by a data processing module so as to obtain a plurality of processed ECG signal data, and the reference data pre-processing step includes Step 221, Step 222, Step 223 and Step 224. Step 221 and Step 222 are the same as Step 121 and Step 122 of the method 100 for establishing heart failure assessment program of FIG. 1, so that the same details will not be described again herein.

In Step 223, a signal transforming step is performed, wherein each of the reference ECG signal data is processed by the data processing module with a signal transforming method so as to obtain a plurality of vectorcardiography data. In detail, in the signal transforming step, each of the reference ECG signal data is transformed to a vectorcardiography data by an inversion equation of Dower so as to process the following analysis. In detail, in the inversion equation of Dower, the 12-lead electrocardiogram data is used as the reference ECG signal data, and then Lead I, Lead II, Lead V1, Lead V2, Lead V3, Lead V4, Lead V5 and Lead V6 of the 12-lead electrocardiogram data will be transformed to the vectorcardiography data according to the following formulas:

$$V=AM,$$

wherein V is the vectorcardiography data, which is composed by X vector, Y vector and Z vector, A is a transformation matrix, and M is a matrix composed by Lead V1, Lead V2, Lead V3, Lead V4, Lead V5, Lead V6, Lead I and Lead II of the reference ECG signal data.

In Step 224, a cardiac axis correcting step is performed, wherein each of the vectorcardiography data is analyzed by the data processing module so as to obtain a cardiac axial vector, and then each of the vectorcardiography data is normalized based on the cardiac axial vector so as to obtain the plurality of processed ECG signal data. In detail, after each of the reference ECG signal data is transformed to the vectorcardiography data, the vectorcardiography data will be automatically analyzed by the data processing module so as to define a vector direction as a target axis. After the target axis is obtained, two additional axes will be defined so as to keep more features of the vectorcardiography data. In the definition of the additional axes, all of the vector data of the vectorcardiography data will be projected on a plane of the target axis by the data processing module, and then all of the vector data will be averaged so as to obtain an average vector direction. Then, the average vector direction and the target axis are used to estimate another vertical vector in the three-dimensional space, and the another vertical vector is served as a first additional axis. Then, another vertical vector between the target axis and the first additional axis is estimated so as to obtain a second additional axis. Finally, the cardiac axial vector will be projected on the target axis and the two additional axes by the data processing module so as to correct the direction of the cardiac axis of each of the vectorcardiography data, and the processed ECG signal data corresponding to each of the reference ECG signal data can be obtained.

Therefore, by pre-processing the plurality of reference ECG signal data of the heart failure patients and analyzing the features thereof, the method 100 for establishing heart failure assessment program and the method 200 for establishing heart failure assessment program of the present disclosure can remove the background noise from each of the reference ECG signal data, and the characteristic intensity of the reference ECG signal data in time and in space also can be enhanced. Further, the reference ECG signal data are analyzed and trained by the machine learning algorithm model so as to establish the heart failure assessment program of the present disclosure, so that the heart failure assessment program of the present disclosure can be used to assess whether a subject has a heart failure or not and a severity of the heart failure and have excellent clinical application convenience and versatility.

[Method for Assessing Occurrence of Heart Failure of the Present Disclosure]

Figure 3:
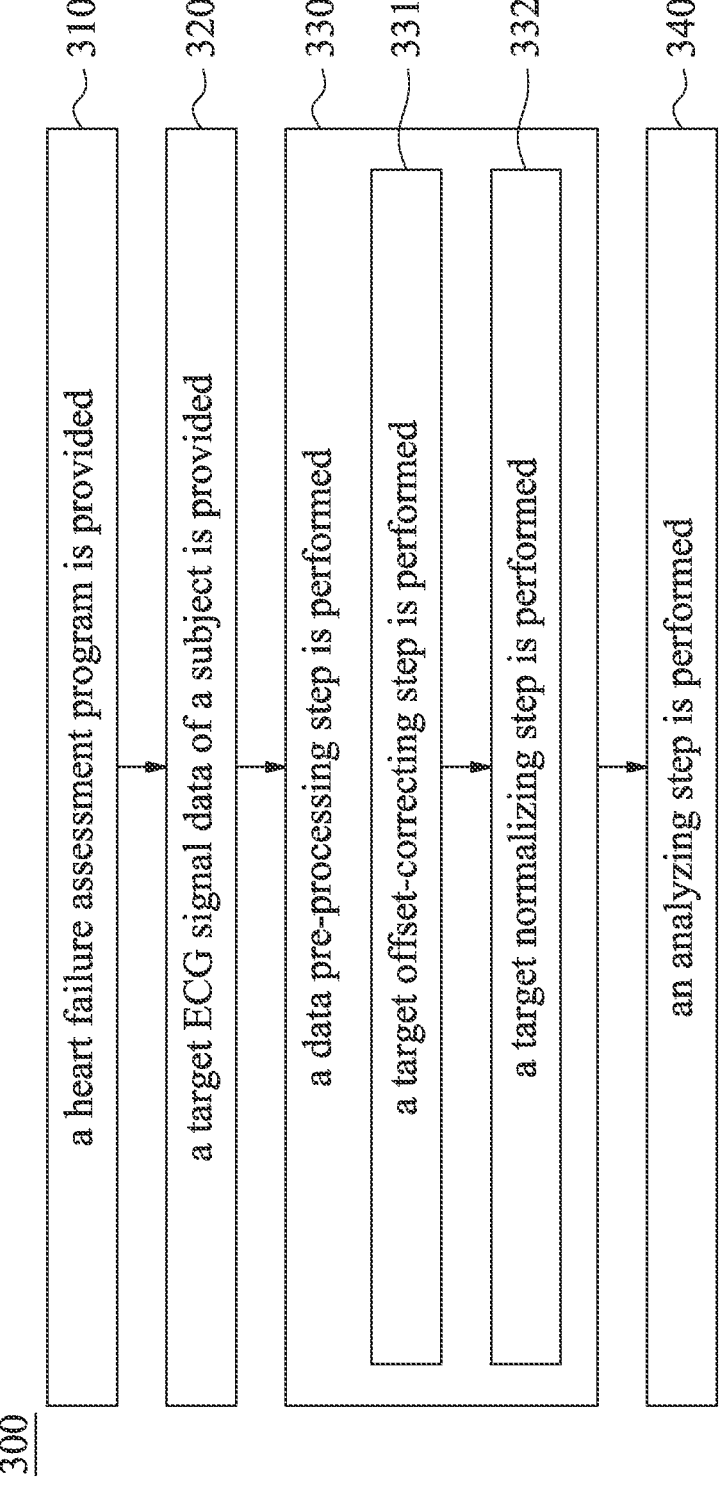
FIG. 3 is a flow chart of a method for assessing occurrence of heart failure according to another embodiment of the present disclosure.

Reference is made to FIG. 3, which is a flow chart of a method 300 for assessing occurrence of heart failure according to another embodiment of the present disclosure. The method 300 for assessing occurrence of heart failure includes Step 310, Step 320, Step 330 and Step 340.

In Step 310, a heart failure assessment program is provided, and the heart failure assessment program is established by the method 100 for establishing heart failure assessment program or the method 200 for establishing heart failure assessment program of the present disclosure.

In Step 320, a target ECG signal data of a subject is provided, wherein the target ECG signal data includes a plurality of target heartbeat waveform data and a plurality of target heart rate data, and each of the target heartbeat waveform data corresponds to one of the target heart rate data. Further, the target ECG signal data can be obtained closest to the time when the subject received a cardiac ultrasound examination, but the present disclosure is not limited thereto. Furthermore, the target ECG signal data can be a 12-lead electrocardiogram data, and the present disclosure is not limited thereto.

In Step 330, a data pre-processing step is performed, wherein the target ECG signal data is pre-processed by a data processing module so as to obtain a processed target ECG signal data. In particular, the data pre-processing step can include Step 331 and Step 332.

In Step 331, a target offset-correcting step is performed, wherein a baseline of the target ECG signal data is adjusted based on the plurality of target heart rate data corresponding thereto so as to eliminate the interference caused by the offsets of the baseline during the examination. Further, the definitional details of the target offset-correcting step are the same as that of Step 121, and the only difference is that the target ECG signal data of the subject is processed in the target offset-correcting step. Thus, the same details will not be described again herein.

In Step 332, a target normalizing step is performed, wherein the target ECG signal data is processed by an interpolation method so as to obtain the processed target ECG signal data. In detail, in the target ECG signal data, there is a plurality of heartbeats within a 10-second period in each of the target ECG signal data, and although the repeatability of the waveforms of different heartbeats is very high, there are still slight differences between the waveforms of different heartbeats. Thus, in the target normalizing step, all of the heart rate data in the target ECG signal data will be averaged by the interpolation method so as to obtain a normalized target heart rate data, and the normalized target heart rate data obtained therefrom will be used as a heart rate value of the target ECG signal data so as to normalize all of the heartbeat waveform data thereof. Then, each of the heartbeat waveform data of the target ECG signal data will be separated out, and all of the heartbeat waveform data will be averaged so as to obtain a normalized target heartbeat waveform data. Finally, the normalized target heartbeat waveform data is defined as one heartbeat of the target ECG signal data, and then the processed target ECG signal data with a specific heartbeat pattern is obtained. Further, the interpolation method can be a cubic spline function interpolation method, and the data processing module can be any of the data processing modules which can be used to analyze and perform the aforementioned processes to the target ECG signal data, and the present disclosure is not limited thereto.

In Step 340, an analyzing step is performed, wherein the processed target ECG signal data is analyzed by the heart failure assessment program so as to obtain a heart failure occurrence assessing result, and the heart failure occurrence assessing result presents a heart failure occurring condition and the severity of the heart failure of the subject.

Figure 4:
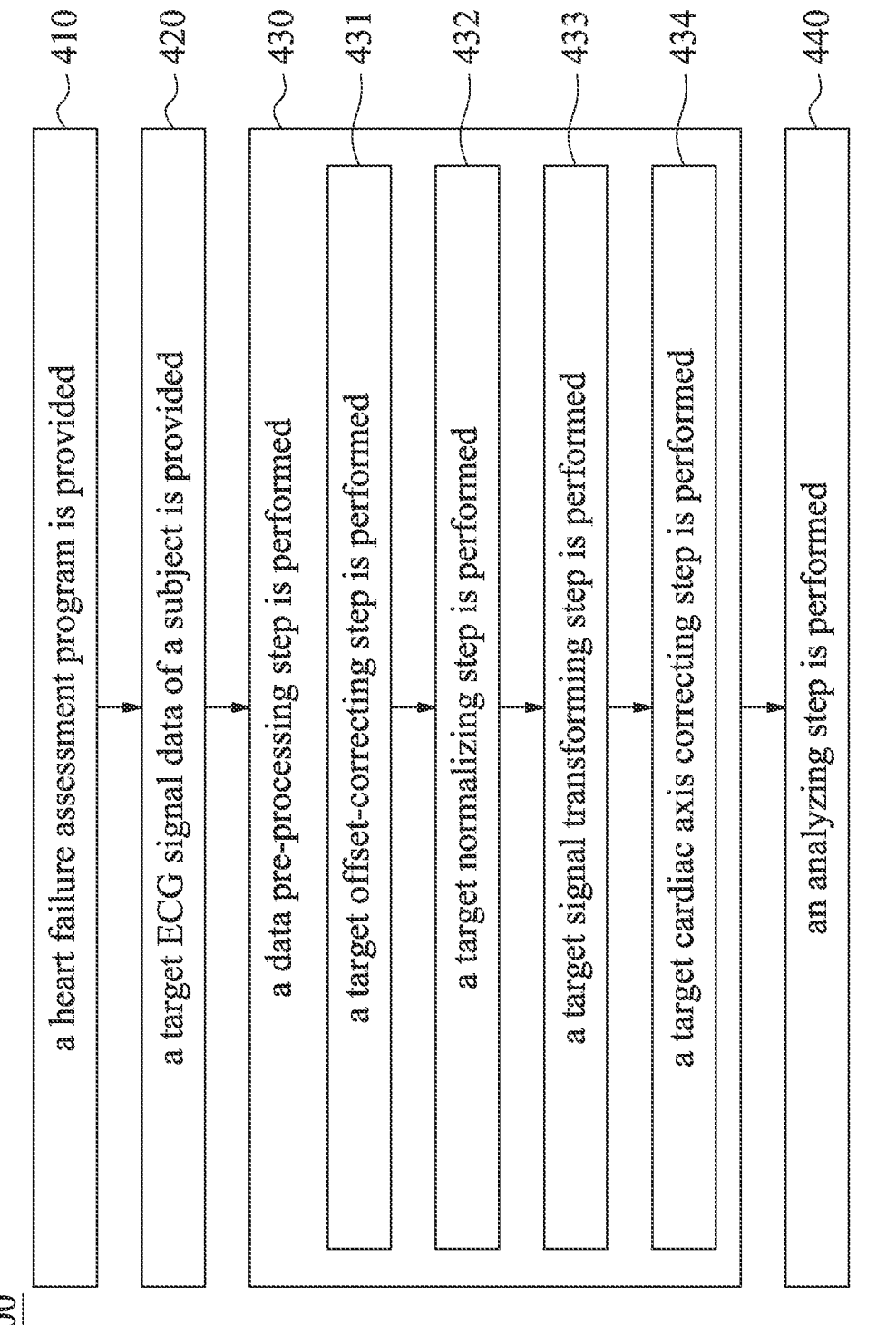
FIG. 4 is a flow chart of a method for assessing occurrence of heart failure according to another embodiment of the present disclosure.

Reference is made to FIG. 4, which is a flow chart of a method 400 for assessing occurrence of heart failure according to another embodiment of the present disclosure. The method 400 for assessing occurrence of heart failure includes Step 410, Step 420, Step 430 and Step 440, wherein Step 410, Step 420 and Step 440 are the same as Step 310, Step 320 and Step 340 of the method 300 for assessing occurrence of heart failure of FIG. 3, so that the same details will not be described again herein.

In Step 430, a data pre-processing step is performed, wherein the target ECG signal data is pre-processed by the data processing module so as to obtain a processed target ECG signal data, and the data pre-processing step includes Step 431, Step 432, Step 433 and Step 434. Step 431 and Step 432 are the same as Step 331 and Step 332 of the method 300 for assessing occurrence of heart failure of FIG. 3, so that the same details will not be described again herein.

In Step 433, a target signal transforming step is performed, wherein the target ECG signal data is processed by the data processing module with a signal transforming method so as to obtain a target vectorcardiography data. In the target signal transforming step, the target ECG signal data is transformed to a target vectorcardiography data by an inversion equation of Dower so as to process the following analysis. The details of the inversion equation of Dower are shown in the description of Step 223, so that it will not be described herein again.

In Step 434, a target cardiac axis correcting step is performed, wherein the target vectorcardiography data is analyzed by the data processing module so as to obtain a target cardiac axial vector, and then the target ECG signal data is normalized based on the target cardiac axial vector so as to obtain the processed target ECG signal data. In detail, after the target ECG signal data is transformed to the target vectorcardiography data, the vectorcardiography data will be automatically analyzed by the data processing module so as to define a vector direction as a target axis and two additional axes. Then, the target cardiac axial vector will be projected on the target axis and the two additional axes by the data processing module so as to correct the direction of the cardiac axis of the target vectorcardiography data. Further, the definitional details of the additional axes are the same as that of Step 224, and the only difference is that the target ECG signal data of the subject is processed in the cardiac axis correcting step. Thus, the same details will not be described again herein.

Therefore, by analyzing the target ECG signal data by the failure assessment program of the present disclosure and then outputting the heart failure occurrence assessing result, the method 300 for assessing occurrence of heart failure and the method 400 for assessing occurrence of heart failure of the present disclosure can effectively and accurately assess whether the subject has a heart failure or not and a severity of the heart failure. Thus, it is favorable for planning the following medical treatments in advance and preventing the patient's health from being affected by the deterioration of the illness condition.

Example

The ECG signal data used in the present example are 50,900 of 12-lead electrocardiogram data of the heart failure patients collected by China Medical University Hospital. The types of the heart failure are defined according to the ejection fraction values and the SE/EACVI 2016 algorithm and then classified as the systolic dysfunction and the diastolic dysfunction. One of the heart failure patients can correspond to plural of the ECG signal data, and the ECG signal data obtained closest to the time when the patient received a cardiac ultrasound examination is selected for the following analysis.

The heart failure assessment program established by the method for establishing heart failure assessment program of the present disclosure will be used in the following tests along with the method for assessing occurrence of heart failure of the present disclosure so as to assess the accuracy of the method for assessing occurrence of heart failure of the present disclosure used to assess the occurrence of heart failure. The heart failure assessment program of the present disclosure can be established by the method 100 for establishing heart failure assessment program or the method 200 for establishing heart failure assessment program, and the method for assessing occurrence of heart failure can be the method 300 for assessing occurrence of heart failure or the method 400 for assessing occurrence of heart failure, so that the same details will not be described again herein.

Before using to establish the heart failure assessment program, the ECG signal data will be processed by the pre-processing step and the feature analyzing step. In detail, each of the ECG signal data will be pre-processed by the reference data pre-processing step so as to remove the background noise of each of the ECG signal data and eliminate the sampling differences between different ECG signal data. In the feature analyzing step, the best parameter combination used to train or select the model is obtained by repeatedly testing different combinations of the parameter.

Figures 5A, 5B:
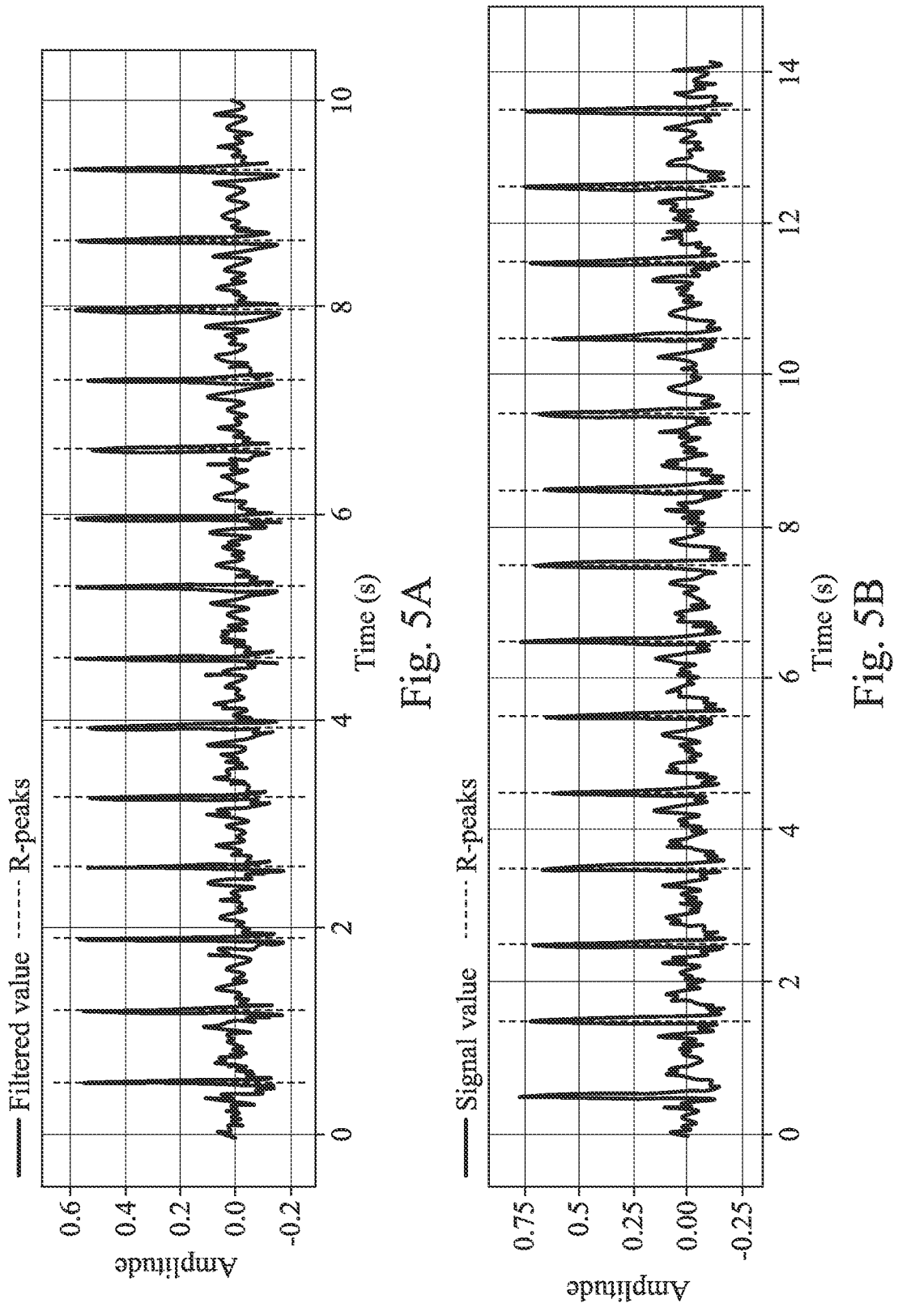
FIG. 5A shows an ECG signal data.
FIG. 5B shows an ECG signal data obtained from the ECG signal data of FIG. 5A after processed by a reference data pre-processing step.

Reference is made to FIG. 5A and FIG. 5B. FIG. 5A shows an ECG signal data, and FIG. 5B shows an ECG signal data obtained from the ECG signal data of FIG. 5A after processed by a reference data pre-processing step. As shown in FIG. 5A and FIG. 5B, after the processing of the reference data pre-processing step, the background noise of the ECG signal data is significantly reduced, and the position of the baseline, the amplitude and the waveform of different heartbeats will be more consistent.

Figures 6A, 6B:
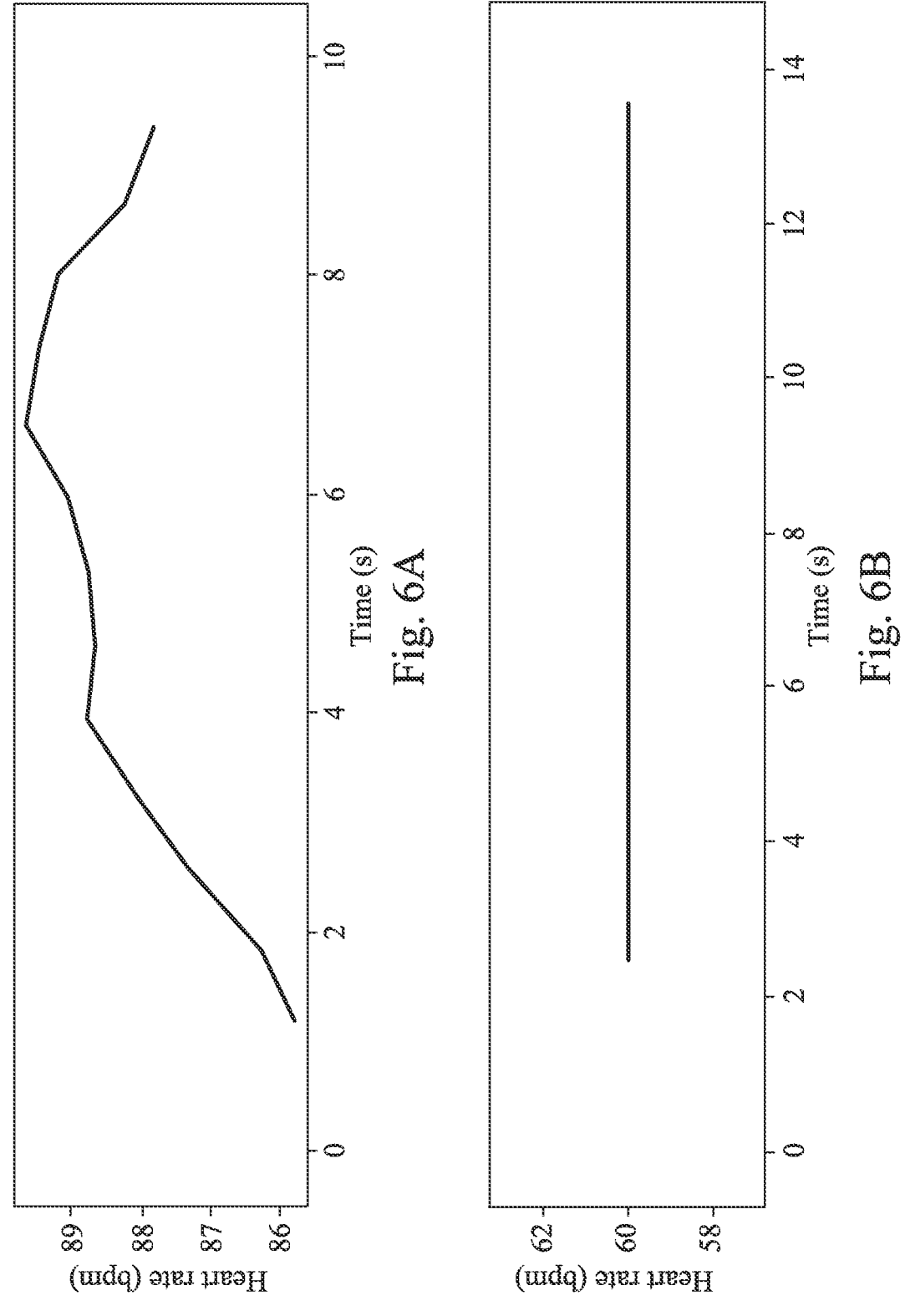
FIG. 6A shows a heart rate data corresponding to the ECG signal data of FIG. 5A.
FIG. 6B shows a normalized heart rate data obtained from the heart rate data of FIG. 6A after processed by a reference data pre-processing step.

Reference is made to FIG. 6A and FIG. 6B. FIG. 6A shows a heart rate data corresponding to the ECG signal data of FIG. 5A, and FIG. 6B shows a normalized heart rate data obtained from the heart rate data of FIG. 6A after processed by a reference data pre-processing step. As shown in FIG. 6A, before the processing of the reference data pre-processing step, the value of the heart rate data corresponding to the ECG signal data changes greatly. However, as shown in FIG. 6B, after being averaged by the interpolation method to all of the heart rate data, the value of the heart rate of the normalized heart rate data is normalized to 60 bpm, and all of the heartbeat waveforms will be accordingly normalized based thereon.

Figures 7A, 7B:
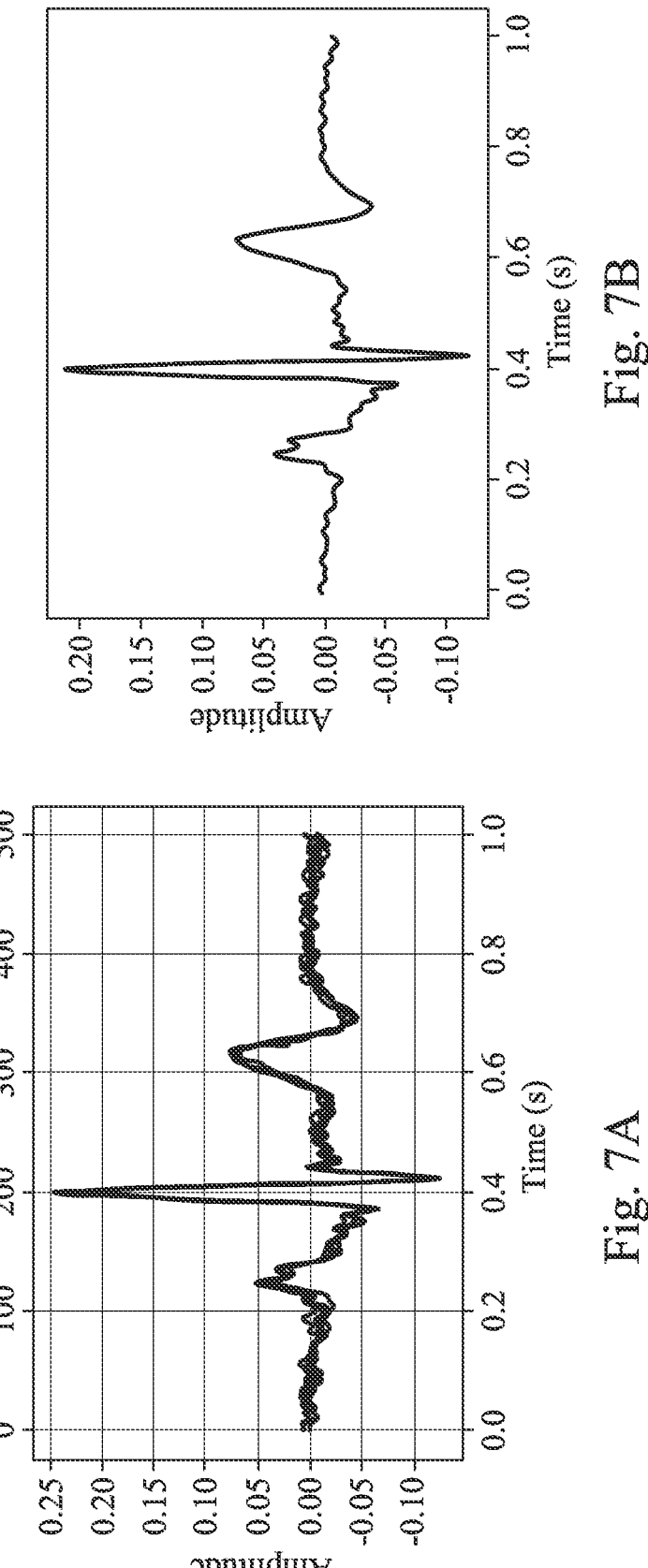
FIG. 7A shows a result of the ECG signal data of FIG. 5B after processed by a feature analyzing step.
FIG. 7B shows a result of the data of FIG. 7A after processed by the feature analyzing step.
Figure 7C:
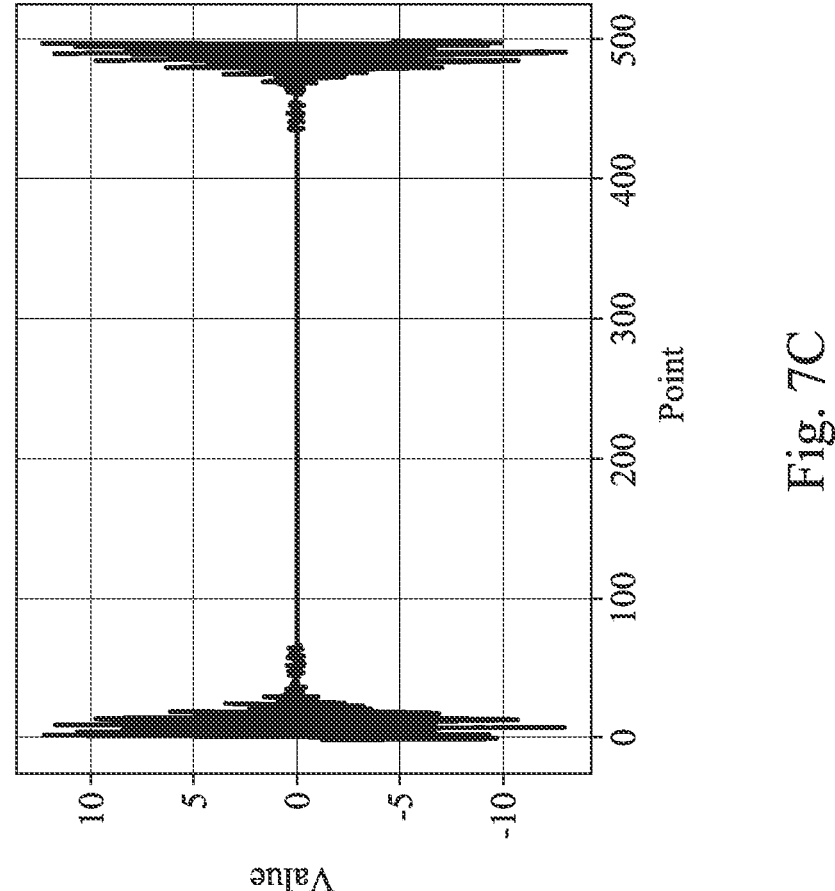
FIG. 7C shows a result of the data of FIG. 7B after processed by the feature analyzing step.

Reference is further made to FIG. 5B, FIG. 7A, FIG. 7B and FIG. 7C simultaneously, wherein FIG. 7A shows a result of the ECG signal data of FIG. 5B after processed by a feature analyzing step, FIG. 7B shows a result of the data of FIG. 7A after processed by the feature analyzing step, and FIG. 7C shows a result of the data of FIG. 7B after processed by the feature analyzing step.

As shown in FIG. 7A, FIG. 7B and FIG. 7C, after the ECG signal data without the background noise of FIG. 5B is processed by the feature analyzing step, the signals of the ECG signal data can be transmitted based on the change between the time domain and the frequency domain, and then the heart failure assessing features that can be used to established the heart failure assessment program can be obtained.

Reference is made to Table 1, which shows the verification results of the heart failure assessment program used to assess the occurrence of heart failure, wherein the heart failure assessment program is established based on a machine learning algorithm model by training different parameter combinations, and the machine learning algorithm model is a gradient descent algorithm model. In the present example, the gradient descent algorithm mode is XGBoost machine learning algorithm model.

TABLE 1

| Target | Systolic Dysfunction | Diastolic Dysfunction |
|---|---|---|
| Accuracy | 0.81~0.92 | 0.79~0.87 |
| AUC | 0.76~0.85 | 0.75~0.81 |
| Sensitivity | 0.67~0.77 | 0.67~0.74 |
| Specificity | 0.83~0.93 | 0.81~0.88 |
| NPV | 0.94~0.99 | 0.94~0.97 |

As shown in Table 1, all of the accuracy, the sensitivity and the specificity for assessing the occurrence of heart failure of the subject of the heart failure assessment program established by different parameter combinations are excellent, the NPV (negative predictive value) approaches 1, and the AUC (Area Under the Receiver Operating Characteristic curve) thereof are up to 0.70 or more. Therefore, the method for assessing occurrence of heart failure of the present disclosure can be used to assess the occurrence of heart failure accurately based on the ECG signal data of a subject, and the present disclosure has excellent clinical application potential.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure covers modifications and variations of this disclosure provided they fall within the scope of the following claims.

What is claimed is:

1. A method for establishing a heart failure assessment program, comprising:

providing an ECG (electrocardiogram) signal database, wherein the ECG signal database comprises a plurality of reference ECG signal data of a plurality of heart failure patients, each of the reference ECG signal data comprises a plurality of heartbeat waveform data and a plurality of heart rate data, and each of the plurality of heartbeat waveform data corresponds to one of the plurality of heart rate data;

performing a reference data pre-processing step, wherein each of the plurality of reference ECG signal data is pre-processed so as to obtain a plurality of processed ECG signal data, and the reference data pre-processing step comprises:

performing an offset-correcting step, wherein a baseline of each of the plurality of reference ECG signal data is adjusted based on the plurality of heart rate data corresponding thereto; and performing a normalizing step, wherein each of the plurality of reference ECG signal data processed by the offset-correcting step is processed by an interpolation method so as to obtain the plurality of processed ECG signal data;

performing a feature analyzing step, wherein the plurality of processed ECG signal data are analyzed by a machine learning algorithm model so as to obtain at least one heart failure assessing feature; and performing a training step, wherein the machine learning algorithm model is trained by the at least one heart failure assessing feature so as to obtain the heart failure assessment program, and the heart failure assessment program is for assessing whether a subject has a heart failure or not and a severity of the heart failure.

2. The method for establishing the heart failure assessment program of claim 1, wherein each of the plurality of reference ECG signal data is a 12-lead electrocardiogram data.

3. The method for establishing the heart failure assessment program of claim 1, wherein the plurality of heart rate data of each of the plurality reference ECG signal data are processed by the interpolation method in the normalizing step so as to obtain a normalized heart rate data, and the normalized heart rate data is used to normalize the plurality of heartbeat waveform data of each of the plurality reference ECG signal data.

4. The method for establishing the heart failure assessment program of claim 3, wherein the interpolation method is a cubic spline function interpolation method.

5. The method for establishing the heart failure assessment program of claim 1, wherein the machine learning algorithm model is a gradient descent algorithm model.

6. The method for establishing the heart failure assessment program of claim 1, wherein the plurality of processed ECG signal data are analyzed by the machine learning algorithm model with a grid search method so as to obtain the at least one heart failure assessing feature.

7. The method for establishing the heart failure assessment program of claim 6, wherein the plurality of processed ECG signal data are further analyzed by the machine learning algorithm model with a cross validation method so as to obtain the at least one heart failure assessing feature.

8. The method for establishing the heart failure assessment program of claim 1, wherein the reference data pre-processing step further comprises:

performing a signal transforming step, wherein each of the plurality of reference ECG signal data is processed with a signal transforming method so as to obtain a plurality of vectorcardiography data; and performing a cardiac axis correcting step, wherein each of the plurality of vectorcardiography data is analyzed so as to obtain a cardiac axial vector, and then each of the plurality of vectorcardiography data is normalized based on the cardiac axial vector so as to obtain the plurality of processed ECG signal data.

9. The method for establishing the heart failure assessment program of claim 8, wherein the signal transforming method uses a 12-lead electrocardiogram data is used as the plurality of reference ECG signal data and a Lead I, a Lead II, a Lead V1, a Lead V2, a Lead V3, a Lead V4, a Lead V5 and a Lead V6 of the 12-lead electrocardiogram data are transformed to the plurality of vectorcardiography data according to the following formulas:

V=AM, wherein V is one of the plurality of vectorcardiography data, which is composed by X vector, Y vector and Z vector, A is a transformation matrix, and M is a matrix composed by the Lead V1, the Lead V2, the Lead V3, the Lead V4, the Lead V5, the Lead V6, the Lead I and the Lead II.

10. A method for assessing occurrence of heart failure, comprising:

providing the heart failure assessment program established by the method for establishing heart failure assessment program of claim 1;

providing a target ECG signal data of the subject, wherein the target ECG signal data comprises a plurality of target heartbeat waveform data and a plurality of target heart rate data, and each of the plurality of target heartbeat waveform data corresponds to one of the plurality of target heart rate data;

performing a data pre-processing step, wherein the target ECG signal data is pre-processed so as to obtain a processed target ECG signal data, and the data pre-processing step comprises:

performing a target offset-correcting step, wherein a baseline of the target ECG signal data is adjusted based on the plurality of target heart rate data corresponding thereto; and performing a target normalizing step, wherein the target ECG signal data processed by the offset-correcting step is processed by the interpolation method so as to obtain the processed target ECG signal data; and performing an analyzing step, wherein the processed target ECG signal data is analyzed by the heart failure assessment program so as to obtain a heart failure occurrence assessing result, and the heart failure occurrence assessing result presents a heart failure occurring condition and the severity of the heart failure of the subject.

11. The method for assessing occurrence of heart failure of claim 10, wherein the target ECG signal data is a 12-lead electrocardiogram data.

12. The method for assessing occurrence of heart failure of claim 10, wherein the plurality of target heart rate data of the target ECG signal data are processed by the interpolation method in the target normalizing step so as to obtain a normalized target heart rate data, and the normalized target heart rate data is used to normalize the plurality of target heartbeat waveform data of the target ECG signal data.

13. The method for assessing occurrence of heart failure of claim 12, wherein the interpolation method is a cubic spline function interpolation method.

14. The method for assessing occurrence of heart failure of claim 10, wherein the data pre-processing step further comprises:

performing a target signal transforming step, wherein the target ECG signal data is processed so as to obtain a target vectorcardiography data; and performing a target cardiac axis correcting step, wherein the target vectorcardiography data is analyzed so as to obtain a target cardiac axial vector, and then the target ECG signal data is normalized based on the target cardiac axial vector so as to obtain the processed target ECG signal data.

15. The method for assessing occurrence of heart failure of claim 14, wherein the signal transforming method is an inversion equation of Dower uses and a 12-lead electrocardiogram data is used as the target ECG signal data and a Lead I, a Lead II, a Lead V1, a Lead V2, a Lead V3, a Lead V4, a Lead V5 and a Lead V6 of the 12-lead electrocardiogram data is transformed to the target vectorcardiography data according to the following formulas:

V=AM, wherein V is the target vectorcardiography data, which is composed by X vector, Y vector and Z vector, A is a transformation matrix, and M is a matrix composed by the Lead V1, the Lead V2, the Lead V3, the Lead V4, the Lead V5, the Lead V6, the Lead I and the Lead II.

*    *    *    *    *